United States Patent
Armstrong et al.

(10) Patent No.: US 7,769,455 B2
(45) Date of Patent: Aug. 3, 2010

(54) POWER SUPPLY MONITORING FOR AN IMPLANTABLE DEVICE

(75) Inventors: Randolph Armstrong, Houston, TX (US); Scott A. Armstrong, Danbury, TX (US); Dana Michael Inman, Seabrook, TX (US); Timothy Scott, Sugar Land, TX (US)

(73) Assignee: Cyberonics, Inc., Houston, TX (US)

( * ) Notice: Subject to any disclaimer, the term of this patent is extended or adjusted under 35 U.S.C. 154(b) by 746 days.

(21) Appl. No.: 11/341,978

(22) Filed: Jan. 27, 2006

(65) Prior Publication Data

US 2007/0179547 A1   Aug. 2, 2007

(51) Int. Cl.
*A61N 1/00* (2006.01)
(52) U.S. Cl. ...................................... 607/29
(58) Field of Classification Search .............. 607/5, 607/27, 29; 320/132; 340/636.15; 702/63
See application file for complete search history.

(56) References Cited

U.S. PATENT DOCUMENTS

| | | | |
|---|---|---|---|
| 3,796,221 A | 3/1974 | Hagfors | |
| 4,324,251 A * | 4/1982 | Mann .......................... | 607/30 |
| 4,488,555 A | 12/1984 | Imran | |
| 4,556,061 A | 12/1985 | Barreras et al. | |
| 4,686,990 A | 8/1987 | Moberg | |
| 4,715,381 A | 12/1987 | Moberg | |
| 4,850,356 A | 7/1989 | Heath | |
| 4,899,750 A | 2/1990 | Ekwall | |
| 4,964,407 A | 10/1990 | Baker, Jr. et al. | |
| 5,137,020 A | 8/1992 | Wayne et al. | |
| 5,137,021 A | 8/1992 | Wayne et al. | |
| 5,146,920 A | 9/1992 | Yuuchi et al. | |
| 5,154,172 A | 10/1992 | Terry, Jr. et al. | |
| 5,179,950 A | 1/1993 | Stanislaw | |

(Continued)

FOREIGN PATENT DOCUMENTS

| WO | WO 0108749 | 2/2001 |
|---|---|---|
| WO | WO2004075982 A1 | 9/2004 |

OTHER PUBLICATIONS

Armstrong, Randolph K., et al., U.S. Appl. No. 10/902,221, filed Jul. 28, 2004, 71 pages (including 13 sheets of Formal Drawings).

(Continued)

*Primary Examiner*—Mark W Bockelman
*Assistant Examiner*—Roland Dinga
(74) *Attorney, Agent, or Firm*—Conley Rose, P.C.

(57) ABSTRACT

A method and an apparatus for projecting an end of service (EOS) and/or an elective replacement indication (ERI) of a component in an implantable device is provided. The method comprises measuring the measured voltage of the energy storage device, and determining whether the measured voltage is less than a transition voltage. When the measured voltage is less than the transition voltage, determining a time period remaining until an end of service of the energy storage device is based upon a function of the measured voltage. When the measured voltage is greater than or equal to the transition voltage, determining a time period remaining until an end of service of the energy storage device is based upon a function of the total charge depleted. The transition voltage is a voltage associated with the transition point of non-linearity in the battery voltage depletion curve.

7 Claims, 7 Drawing Sheets

U.S. PATENT DOCUMENTS

| | | | |
|---|---|---|---|
| 5,193,538 | A | 3/1993 | Ekwall |
| 5,201,808 | A | 4/1993 | Steinhaus et al. |
| 5,201,865 | A | 4/1993 | Kuehn |
| 5,222,494 | A | 6/1993 | Baker, Jr. |
| 5,344,431 | A | 9/1994 | Merritt et al. |
| 5,352,968 | A | 10/1994 | Reni et al. .................... 320/35 |
| 5,391,193 | A | 2/1995 | Thompson |
| 5,431,692 | A | 7/1995 | Hansen et al. |
| 5,458,624 | A | 10/1995 | Renirie et al. |
| 5,496,353 | A | 3/1996 | Grandjean et al. |
| 5,507,786 | A | 4/1996 | Morgan et al. |
| 5,522,865 | A | 6/1996 | Schulman et al. |
| 5,534,018 | A | 7/1996 | Wahlstrand et al. |
| 5,549,646 | A | 8/1996 | Katz et al. |
| 5,620,474 | A | 4/1997 | Koopman |
| 5,713,936 | A | 2/1998 | Staub et al. |
| 5,741,307 | A | 4/1998 | Kroll |
| 5,741,311 | A | 4/1998 | McVenes et al. |
| 5,755,742 | A | 5/1998 | Schuelke et al. |
| 5,769,873 | A | 6/1998 | Zadeh |
| 5,814,088 | A | 9/1998 | Paul et al. |
| 5,876,425 | A | 3/1999 | Gord et al. |
| 5,891,179 | A | 4/1999 | Er et al. |
| 5,897,577 | A | 4/1999 | Cinbis et al. |
| 5,925,068 | A | 7/1999 | Kroll |
| 6,016,448 | A | 1/2000 | Busacker et al. |
| 6,073,050 | A | 6/2000 | Griffith |
| 6,108,579 | A | 8/2000 | Snell et al. |
| 6,148,235 | A | 11/2000 | Kuiper |
| 6,167,309 | A | 12/2000 | Lyden |
| 6,181,969 | B1 | 1/2001 | Gord |
| 6,185,461 | B1 | 2/2001 | Er |
| 6,212,431 | B1 | 4/2001 | Hahn et al. |
| 6,317,633 | B1 | 11/2001 | Jorgenson et al. |
| 6,400,988 | B1 | 6/2002 | Gurewitsch |
| 6,445,951 | B1 | 9/2002 | Mouchawar |
| 6,453,198 | B1 | 9/2002 | Torgerson et al. |
| 6,490,484 | B2 | 12/2002 | Dooley et al. |
| 6,490,486 | B1 | 12/2002 | Bradley |
| 6,553,263 | B1 | 4/2003 | Meadows et al. |
| 6,620,186 | B2 | 9/2003 | Saphon et al. |
| 6,648,823 | B2 | 11/2003 | Thompson |
| 6,654,640 | B2 | 11/2003 | Lyden |
| 6,658,294 | B1 | 12/2003 | Zadeh et al. |
| 6,671,552 | B2 | 12/2003 | Merritt et al. |
| 6,687,538 | B1 | 2/2004 | Hrdlicka et al. |
| 6,721,600 | B2 | 4/2004 | Jorgenson et al. |
| 6,745,077 | B1 | 6/2004 | Griffith et al. |
| 6,748,273 | B1 | 6/2004 | Obel et al. |
| 6,760,624 | B2 | 7/2004 | Anderson et al. |
| 6,760,625 | B1 | 7/2004 | Kroll |
| 6,804,557 | B1 | 10/2004 | Kroll |
| 6,820,019 | B1 | 11/2004 | Kelly et al. |
| 2001/0034541 | A1 | 10/2001 | Lyden .................... 607/29 |
| 2004/0039424 | A1 | 2/2004 | Merritt et al. ................ 607/29 |
| 2004/0199146 | A1* | 10/2004 | Rogers et al. ............ 604/891.1 |
| 2005/0088145 | A1 | 4/2005 | Loch .................... 320/132 |
| 2005/0177206 | A1 | 8/2005 | North et al. |
| 2005/0272280 | A1 | 12/2005 | Osypka |

OTHER PUBLICATIONS

PCT International Searching Authority; Search Report for International Application No. PCT/US2007/000337; 6 pgs.

Terry, R.S., et al., "The Implantable Neurocybernetic Prosthesis System," Pacing and Clinical Electrophysiology, vol. 14, No. 1, (Jan. 1991), pp. 86-93.

Woodbury, J.W., et al., "Vagal Stimulation Reduces the Severity of Maximal Electroshock Seizures in Intact Rats: Use of Cuff Electrode for Stimulating and Recording," PACE, vol. 14, (Jan. 1991), pp. 94-107.

* cited by examiner

POWER SUPPLY MONITORING FOR AN IMPLANTABLE DEVICE

BACKGROUND

1. Technical Field

This disclosure relates generally to implantable medical devices, and more particularly to methods, apparatus, and systems for monitoring power consumption relating to implantable medical devices.

2. Background Information

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated by reference in its entirety in this specification. Electrical stimulation of the vagus nerve may be provided by implanting an electrical device underneath the skin of a patient and electrically stimulating tissue, organ(s) or nerves of the patient. The system may operate without a detection system if the patient has been diagnosed with epilepsy, and may periodically apply a prophylactic series of electrical pulses to the vagus (or other cranial) nerve intermittently throughout the day, or over another predetermined time interval.

Typically, implantable medical devices (IMDs) involving the delivery of electrical pulses to, or sensing electrical activity of, body tissues, such as pacemakers (heart tissue) and vagus nerve stimulators (nerve tissue), comprise a pulse generator for generating the electrical pulses and a lead assembly coupled at its proximal end to the pulse generator terminals and at its distal end to one or more electrodes in contact with the body tissue to be stimulated. One of the key components of such IMDs is the power supply (e.g., a battery), which may or may not be rechargeable. In many cases surgery is required to replace an exhausted battery. Even rechargeable batteries eventually may need replacement. To provide adequate warning of impending depletion of the battery and subsequent degradation of the operation of the IMD, various warning signals or indicators may be established and monitored.

Generally, battery-powered IMDs base warning signals or indicators on battery voltage and/or battery impedance measurements. One problem associated with these methodologies is that, for many battery chemistries, these measured battery characteristics do not have monotonically-changing values with respect to remaining charge. For example, lithium/carbon monofluoride (Li/CFx) cells commonly used in neurostimulators and other IMDs have a relatively flat voltage discharge curve for the majority of their charge life, and present status of the battery cannot be accurately and unambiguously determined from a measured battery characteristic.

More specifically, in LiCFx batteries, the battery voltage remains relatively constant for approximately 90% of its useful life and then reaches a point where the battery changes from a linear region of approximately zero slope to an approximately linear or downwardly curving region of negative slope. Thus, during the last 10% of battery life (when battery voltage versus battery depletion enters the second range), an added term in the projection equation that incorporates battery voltage may improve the accuracy of the projection to the battery's depletion.

Another problem associated with this methodology is the variability of current consumption for a specific device's programmed therapy or circuitry. This variability, combined with the uncertainty of the battery's present status prior to depletion, hinders reliable estimation of the anticipated time until reaching the end of the battery's useful life. For scheduling purposes, it is desirable to have a constantly available and reliable estimate over all therapeutic parameter ranges and operation settings of the time until the device will reach the end of its useful life, and provide an indication when that time reaches a specific value or range.

The present disclosure is directed to overcoming, or at least reducing, the effects of, one or more of the problems set forth above.

BRIEF SUMMARY

In accordance with various embodiments, a method is provided for determining a time period until an end of service of an energy storage device in an implantable medical device, the energy storage device comprising a total available electrical charge that may be obtained from the energy storage device and a measured voltage. The method comprises measuring a measured voltage of the energy storage device and determining whether the measured voltage is less than a transition voltage. When the measured voltage is less than the transition voltage, the method comprises determining a time period remaining in the energy storage device's useful life based upon a function of the measured voltage. When the measured voltage is greater than or equal to the transition voltage, the method comprises determining a time period remaining in the energy storage device's useful life based upon a function of charge depleted.

Still further embodiments are directed to an implantable medical device. The implantable medical device comprises an energy storage device that provides power for an operation performed by the implantable medical device, characterized by a non-linear battery voltage depletion curve of voltage over time, a stimulation unit operatively coupled to the energy storage device that provides an electrical signal; and a controller operatively coupled to the stimulation unit and the energy storage device. The controller comprises a charge depletion determination unit that determines an electrical charge depleted by the energy storage device during operation of the implantable medical device, a voltage determination unit that determines whether a measured voltage across the energy storage device has reached a transition voltage, and a useful life determination unit that determines a time period remaining in the energy storage device's useful life based upon at least one of 1) a function of the electrical charge depleted, and 2) a function of the measured voltage.

Various embodiments are directed to a system for determining remaining useful life of a battery in an implantable medical device. The system comprises an implantable medical device that delivers a stimulation signal to a patient and communicates with an external monitoring device. The implantable device comprises a battery to provide power for an operation performed by the implantable medical device, and a controller operatively coupled to the battery that determines an electrical charge depleted by the battery and a voltage across the battery. The external monitoring device determines, depending on whether the voltage across the battery is less than a transition voltage, a remaining useful life of the battery based upon at least one of (1) the electrical charge depleted and (2) the voltage across the battery. The external monitoring device displays an indication of the remaining useful life of a battery of the implantable medical device.

The preferred embodiments described herein do not limit the scope of this disclosure.

NOTATION AND NOMENCLATURE

Certain terms are used throughout the following description and claims to refer to particular system components. As one skilled in the art will appreciate, implant companies may refer to a components or groups of components by different names. This document does not intend to distinguish between components or groups thereof that differ in name but not function. In the following discussion and in the claims, the terms "including" and "comprising" are used in an open-ended fashion, and thus should be interpreted to mean "including, but not limited to . . . "

BRIEF DESCRIPTION OF THE DRAWINGS

The disclosure may be understood by reference to the following description taken in conjunction with the accompanying drawings, in which like reference numerals identify like elements, and in which.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION

Illustrative embodiments of the disclosure are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present disclosure provide methods and apparatus for monitoring and/or estimating the time remaining until the generation of an elective replacement indicator or until the end of service of the battery of an implantable medical device (IMD). Estimating battery life may be based upon estimated future charge depletion and actual past charge depletion while the battery is operating in a first part of its useful life and on the measured voltage in a second part of its useful life. Specifically, when the battery operates at a voltage greater than or equal to a voltage associated with a transition point of non-linearity in the battery voltage depletion curve shown in FIG. 3 (referred to herein as the knee), estimating the battery life is based on the charge depleted, an example of which is disclosed in U.S. patent application Ser. No. 10/902,221, filed Jul. 28, 2004, incorporated herein by reference in its entirety. When the battery operates at a voltage less than a voltage associated with the knee, estimating the battery life may be determined as a function of measured voltage across the battery, rather than the total charge depleted. Embodiments of the present disclosure provide for the generation an elective replacement indicator (ERI) signal to provide a warning for performing an electrical diagnostic operation upon the IMD. This electrical diagnostic operation may include replacing an electrical component in the IMD, performing additional evaluation(s) of the operation of the IMD, replacing or recharging a power source of the IMD, and the like. A more detailed description of an IMD suitable for use in the present disclosure is provided in various figures and the accompanying description below.

Generally, IMDs contain a power storage device (e.g., a battery) to provide power for the operations of the IMD. Embodiments of the present disclosure determine an estimated usable life remaining in the battery unit based upon where in the battery's useful life it is operating. Embodiments of the present disclosure may be performed in a standalone manner within the IMD itself or in conjunction with an external device in communication with the IMD. Utilizing embodiments of the present disclosure, an end of service (EOS) signal or an elective replacement indicator (ERI) signal may be provided, indicating that the IMD is at or near termination of operations and/or the battery power has reached a level at which replacement should be considered to avoid interruption or loss of therapy to the patient. An ERI signal may indicate that an electrical device component, such as a battery, has reached a point where replacement or recharging is recommended. An EOS signal may provide an indication that the operation of the implanted device is at, or near, termination and delivery of the intended therapy can no longer be guaranteed. ERI and EOS are commonly used indicators of the present status of an IMD battery. ERI is intended to be a warning signal of an impending EOS indication, providing sufficient time (e.g., several weeks or months) in typical applications to schedule and perform the replacement or recharging.

Figure 1:
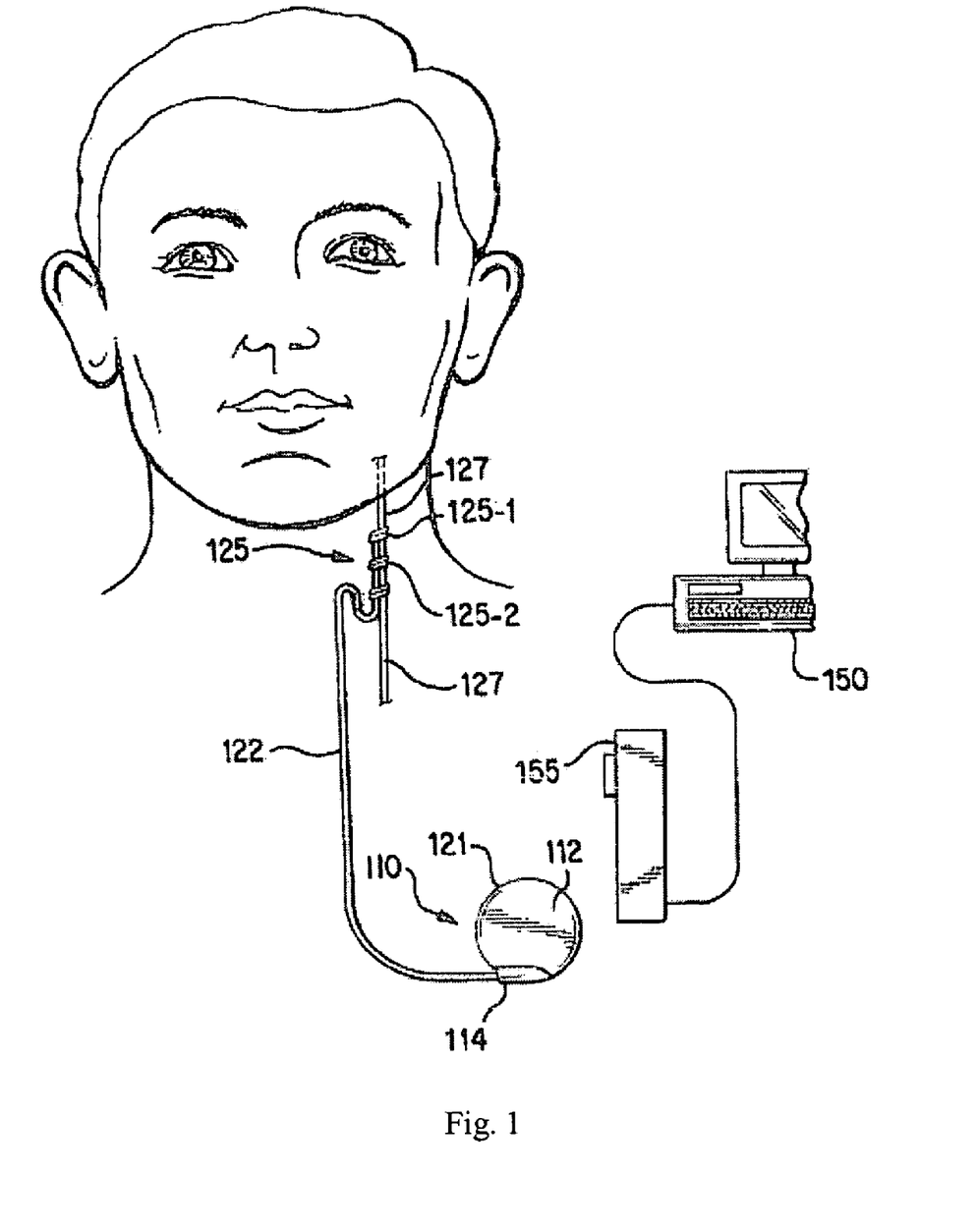
FIG. 1 is a stylized diagram of an implantable medical device suitable for use in the present disclosure implanted into a patient's body and an external programmer.

FIG. 1 illustrates a generator 110 having main body 112 comprising a case or shell 121 with a connector 114 for connecting to leads 122. The generator 110 is implanted in the patient's chest in a pocket or cavity formed by the implanting surgeon just below the skin, similar to the implantation procedure for a pacemaker pulse generator. A stimulating nerve electrode assembly 125, preferably comprising an electrode pair, is conductively connected to the distal end of an insulated electrically conductive lead assembly 122, which preferably comprises a pair of lead wires (one wire for each electrode of an electrode pair). Lead assembly 122 is attached at its proximal end to the connector 114 on case 121. The electrode assembly is surgically coupled to a vagus nerve 127 in the patient's neck. The electrode assembly 125 preferably comprises a bipolar stimulating electrode pair, such as the electrode pair described in U.S. Pat. No. 4,573,481 issued Mar. 4, 1986 to Bullara. Persons of skill in the art will appreciate that many electrode designs could be used in the present disclosure. The two electrodes are preferably wrapped about the vagus nerve, and the electrode assembly 125 is preferably secured to the nerve 127 by a spiral anchoring tether such as that disclosed in U.S. Pat. No. 4,979,511 issued Dec. 25, 1990 to Reese S. Terry, Jr. and commonly owned by the assignee of the instant application. Lead assembly 122 may be secured, while retaining the ability to flex with movement of the chest and neck, by a suture connection to nearby tissue.

The pulse generator 110 may be controlled or programmed with an external device 150 (e.g., a computer) and a programming wand 155 to facilitate radio frequency (RF) communication between the external device 150 and the pulse generator 110. The wand 155 and software permit noninvasive communication with the generator 110 after the latter is implanted.

Figure 2:
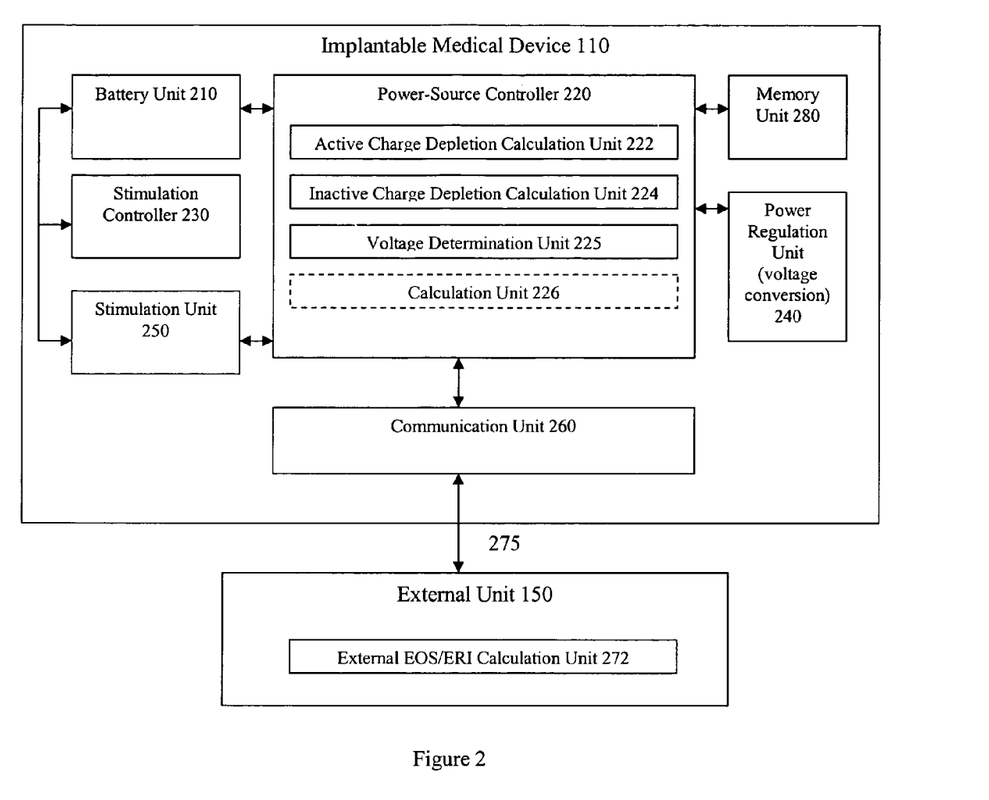
FIG. 2 is a block diagram of an implantable medical device and an external unit that communicates with the implantable medical device, in accordance with one illustrative embodiment of the present disclosure.

FIG. 2 illustrates one embodiment of IMD 110 for performing neurostimulation in accordance with embodiments of the present disclosure. In one embodiment, the implantable medical device 110 comprises a battery unit 210, a power-source controller 220, a stimulation controller 230, a power regulation unit 240, a stimulation unit 250, a memory unit 280 and a communication unit 260. It will be recognized that one or more of the blocks 210-280 (which may also be referred to as modules) may comprise hardware, firmware, software, or any combination thereof. The memory unit 280 may be used for storing various program codes, starting data, and the like. The battery unit 210 comprises a power-source battery that may be rechargeable or non-rechargeable. The battery unit 210 provides power for the operation of the IMD 110, including electronic operations and the stimulation function. The battery unit 210, in one embodiment, may be a lithium/thionyl chloride cell or a lithium/carbon monofluoride cell. The terminals of the battery unit 210 are preferably electrically connected to an input side of the power-source controller 220 and the power regulation unit 240.

The power-source controller 220 preferably comprises circuitry for controlling and monitoring the flow of electrical power to various electronic and stimulation-delivery portions of the IMD 110 (such as the modules 230, 240, 250, 260, and 280 illustrated in FIG. 2). More particularly, the power-source controller 220 is capable of monitoring the power consumption or charge depletion of the implantable medical device 110, measuring the voltage across the battery unit 210, and generating ERI and/or EOS signals. The power-source controller 220 comprises an active charge-depletion unit 222, an inactive charge-depletion unit 224, and a voltage determination unit 225, and an optional calculation unit 226.

The active charge-depletion unit 222 is capable of calculating the charge depletion rate of the implantable medical device 110 while the implantable medical device 110 operates in one or more "active states." Each active state may have an associated charge depletion rate that is the same as or different from at least one other active state. The active state of the implantable medical device 110 refers to a period of time during which a stimulation pulse is delivered by the implantable medical device 110 to body tissue of the patient according to a first set of stimulation parameters. Other active states may include states in which other activities are occurring, such as status checks and/or updates, or stimulation periods according to a second set of stimulation parameters different from the first set of stimulation parameters.

The inactive charge-depletion unit 224 is capable of calculating the charge depletion rate of the implantable medical device 110 during inactive states. Inactive states may comprise various states of inactivity, such as sleep modes, wait modes, and the like.

The voltage determination unit 225 is capable of measuring or receiving the voltage across the battery unit 210 at any given point in time to compare the measured voltage to a transition voltage associated with the transition point of non-linearity on the battery voltage depletion curve (shown in FIG. 3), or the knee. The comparison may be used to determine whether to use the charge depleted, or a function of the measured voltage to determine the time remaining until generation of an ERI or time remaining until EOS. In an embodiment, the voltage determination unit 225 determines whether the voltage across the battery unit 210 is less than the transition voltage associated with the knee. If the battery unit 210 has a measured voltage across it that is greater than or equal to the voltage associated with the knee on the battery voltage depletion curve, the time to ERI or EOS is calculated according to the charge depleted. This calculation may be performed in an external ERI/EOS calculation unit 272 of the external unit 150 after the measured voltage and accumulated charge are communicated from the IMD 110 to the external unit 150. Alternatively, this calculation may be performed in an optional calculation unit 226 of the power-source controller 220, and the result may be communicated from the IMD 110 to the external unit 150.

If the battery unit 210 has a measured voltage that is less than the voltage associated with the knee, the time to ERI or EOS is calculated based on a function of the measured voltage. This calculation may be performed in an external ERI/EOS calculation unit 272 of the external unit 150 after the measured voltage and accumulated charge are communicated from the IMD 110 to the external unit 150. Alternatively, this calculation may be performed in an optional calculation unit 226 of the power-source controller 220, and the result may be communicated from the IMD 110 to the external unit 150. One or more of the active charge-depletion unit 222, the inactive charge-depletion unit 224, and the voltage determination unit 225, the optional calculation unit 226 of the power-source controller 220 and/or the external ERI/EOS calculation unit 272 may be hardware, software, firmware, and/or any combination thereof.

The power regulation unit 240 is capable of regulating the power delivered by the battery unit 210 to particular modules of the IMD 110 according to their needs and functions. The power regulation unit 240 may perform a voltage conversion to provide appropriate voltages and/or currents for the operation of the modules. The power regulation unit 240 may comprise hardware, software, firmware, and/or any combination thereof. The communication unit 260 is capable of providing transmission and reception of electronic signals to and from an external unit 150.

The external unit 150 may be a device that is capable of programming various modules and stimulation parameters of the IMD 110. In one embodiment, the external unit 150 is a computer system capable of electronic communications, programming, and executing a data-acquisition program, preferably a handheld computer or PDA. The external unit 150 is preferably controlled by a healthcare provider such as a physician, at a base station in, for example, a doctor's office. The external unit 150 may be used to download various parameters and program software into the IMD 110 for programming the operation of the implantable device. The external unit 150 may also receive and upload various status conditions and other data from the IMD 110. The communication unit 260 may comprise hardware, software, firmware, and/or any combination thereof. Communications between the external unit 150 and the communication unit 260 may occur via a wireless or other type of communication, illustrated generally by line 275 in FIG. 2.

In an embodiment, the external unit 150 comprises an ERI/EOS calculation unit 272 capable of performing calculations to generate an ERI signal and/or an EOS signal. If the battery unit 210 has a measured voltage across it that is greater than or equal to the voltage associated with the knee on the battery voltage depletion curve (as shown in FIG. 3), the time to ERI or EOS is calculated according to a function of the total charge depleted, and if the battery unit 210 has a measured voltage that is less than the voltage associated with the knee, the time to ERI or EOS is calculated based on a function of the measured voltage. These calculations may be performed either in an optional calculation unit 226 of the power-source controller 220 or in an ERI/EOS calculation unit 272 of the external unit 150. The external ERI/EOS calculation unit 272 may additionally be capable of receiving calculations performed in the optional calculation unit 226 in the IMD 110 that are communicated to the external unit 150. The external ERI/EOS calculation unit 272 may be hardware, software, firmware, and/or any combination thereof.

Stimulation controller 230 defines the stimulation pulses to be delivered to the nerve tissue according to parameters and waveforms that may be programmed into the IMD 110 using the external unit 150. The stimulation controller 230 controls the operation of the stimulation unit 250, which generates the stimulation pulses according to the parameters defined by the controller 230 and in one embodiment provides these pulses to the lead assembly 122 and electrode assembly 125. Various stimulation signals provided by the implantable medical device 110 may vary widely across a range of parameters. The Stimulation controller 230 may comprise hardware, software, firmware, and/or any combination thereof.

Figure 3A:
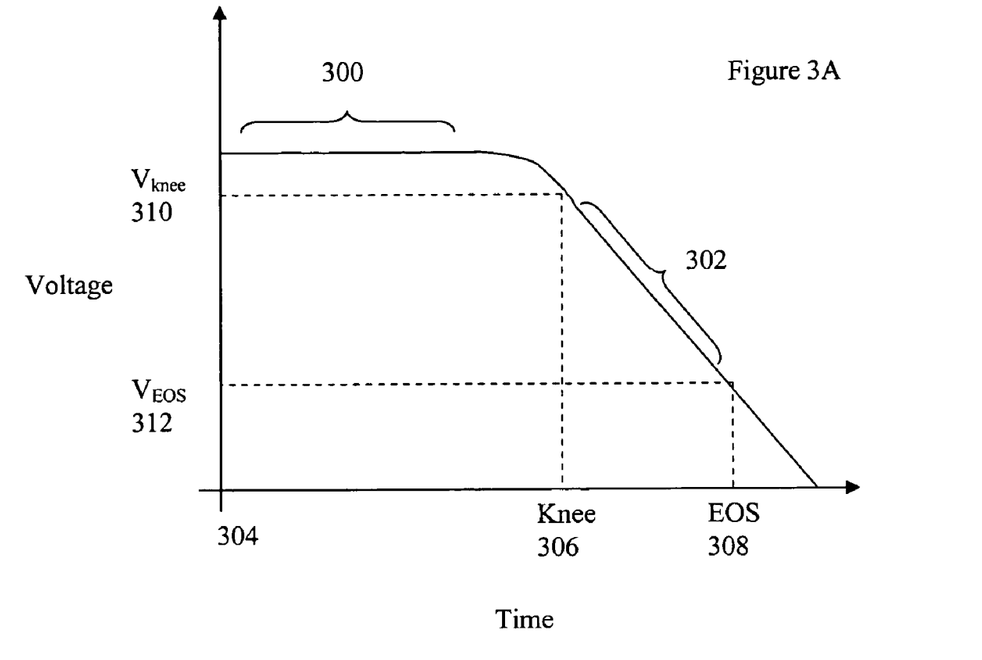
FIG. 3 is a graphical representation of a battery voltage depletion curve typical of an energy storage device or battery, in accordance with one illustrative embodiment of the present disclosure.

FIG. 3A provides a graphical representation of a battery voltage depletion curve in accordance with an embodiment of the present disclosure. The battery voltage depletion curve shown in FIG. 3A is characterized by a first region 300 represented by an approximately linear function having a slope of approximately zero, and a second region 302 represented by an approximately linear function having a negative slope. The first region 300 is defined between the beginning of the life of the battery at time 304 and a time associated with the knee 306. The time associated with the knee 306 corresponds to a transition point along the battery voltage depletion curve between the first region 300 and the second region 302. The time associated with the knee 306 corresponds to a voltage referred to herein as $V_{knee}$ 310. The second region 302 is defined between the time associated with the knee 306 and a time associated with the approximate end of service of the battery 308, a point in time when the battery is no longer effective for powering the IMD 110 for stimulation. The time associated with the approximate end of service of the battery 308 corresponds to a voltage referred to herein as $V_{EOS}$ 312.

Figure 3B:
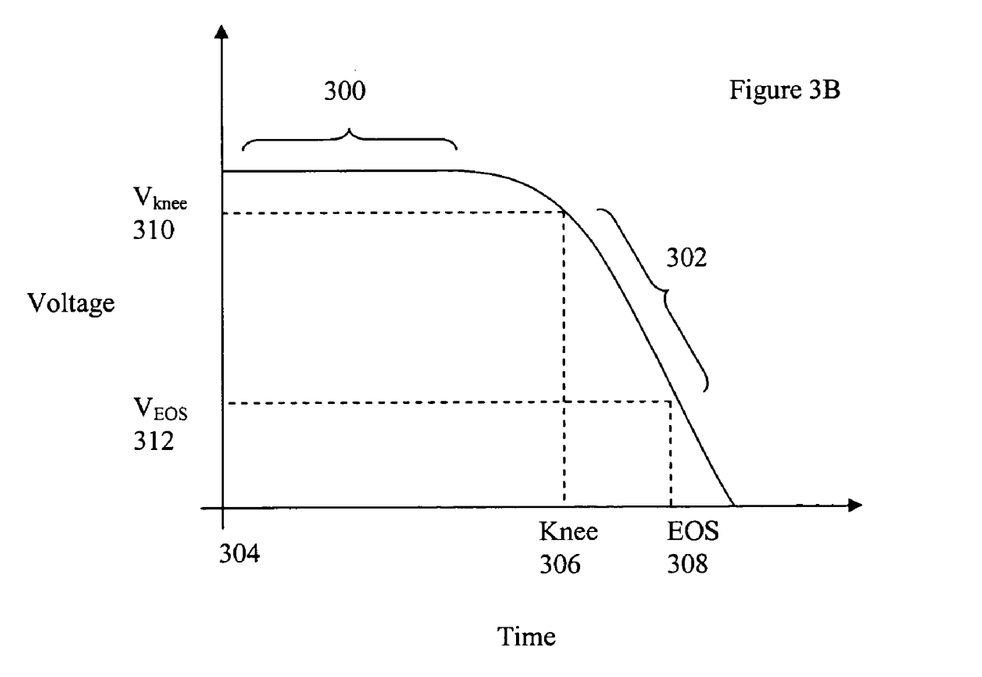

FIG. 3B provides a graphical representation of a battery voltage depletion curve in accordance with another embodiment of the present disclosure. The battery voltage depletion curve shown in FIG. 3B is characterized by a first region 300 represented by an approximately linear function having a slope of approximately zero, and a second region 302 represented by a non-linear approximation comprised of a higher order polynomial with a downwardly curving slope. In a still further embodiment of the present disclosure, the battery voltage depletion curve may be approximated by a non-linear approximation comprised of a higher order polynomial. In such a non-linear approximation, $V_{knee}$ 310 may be selected from various data points along the curve associated with a point in time when the voltage begins to sharply drop.

In one embodiment of the disclosure, the IMD 110 determines EOS and ERI values when the battery unit 210 is in the part of its useful battery life (the first region 300) having voltage greater than or equal to the voltage associated with the knee by using a known initial battery charge ($C_{initial}$) and a predetermined EOS battery charge ($C_{EOS}$) indicative of the end of useful battery service, together with the charge actually depleted ($C_d$) by the IMD (calculated from the present usage rates for idle and stimulation periods ($r_i$ and $r_s$), and the length of the respective idle and stimulation periods), to calculate for a desired time point how much useful charge remains on the battery ($C_r$) until the EOS charge is reached, and how long at projected present usage rates the device can operate until EOS or ERI. Once the charge actually depleted by operation of the device ($C_d$) is known, the present usage rates are then applied to the remaining useful charge $C_r$ to determine the time remaining until EOS and/or ERI.

In one embodiment of the disclosure, the IMD 110 determines EOS and ERI values when the battery unit 210 is in the part of its useful battery life (the second region 302) having voltage less than the voltage associated with the knee by using the measured value for voltage across the battery unit 210, a value for the voltage across the battery unit 210 at the time of EOS (which may be previously set, determined, or programmed into the IMD), a value for the voltage across the battery unit 210 at the knee (which may be previously set, determined, or programmed into the IMD), a constant representing a percentage of battery capacity commonly remaining in the battery when the battery voltage is equal to the voltage associated with the knee (which may be previously set or determined or programmed into the IMD), the known initial battery charge $C_{initial}$, and present usage rates.

In at least some embodiments, EOS and ERI determinations are made without measurements or calculations of internal battery impedance. Instead, in the portion of the battery's useful life (the first region 300) with battery voltage greater than or equal to the voltage associated with the knee, the device maintains a precise record of the current used during idle and stimulation periods, and subtracts the charge represented by the current used from the total available battery charge to determine the charge remaining on the battery. Alternatively, in the portion of the battery's useful life (the second region 302) with the battery voltage less than the voltage associated with the knee, the device bases the time remaining on the measured voltage across the battery, known or predetermined voltage characteristics, and present usage rates.

Figure 4:
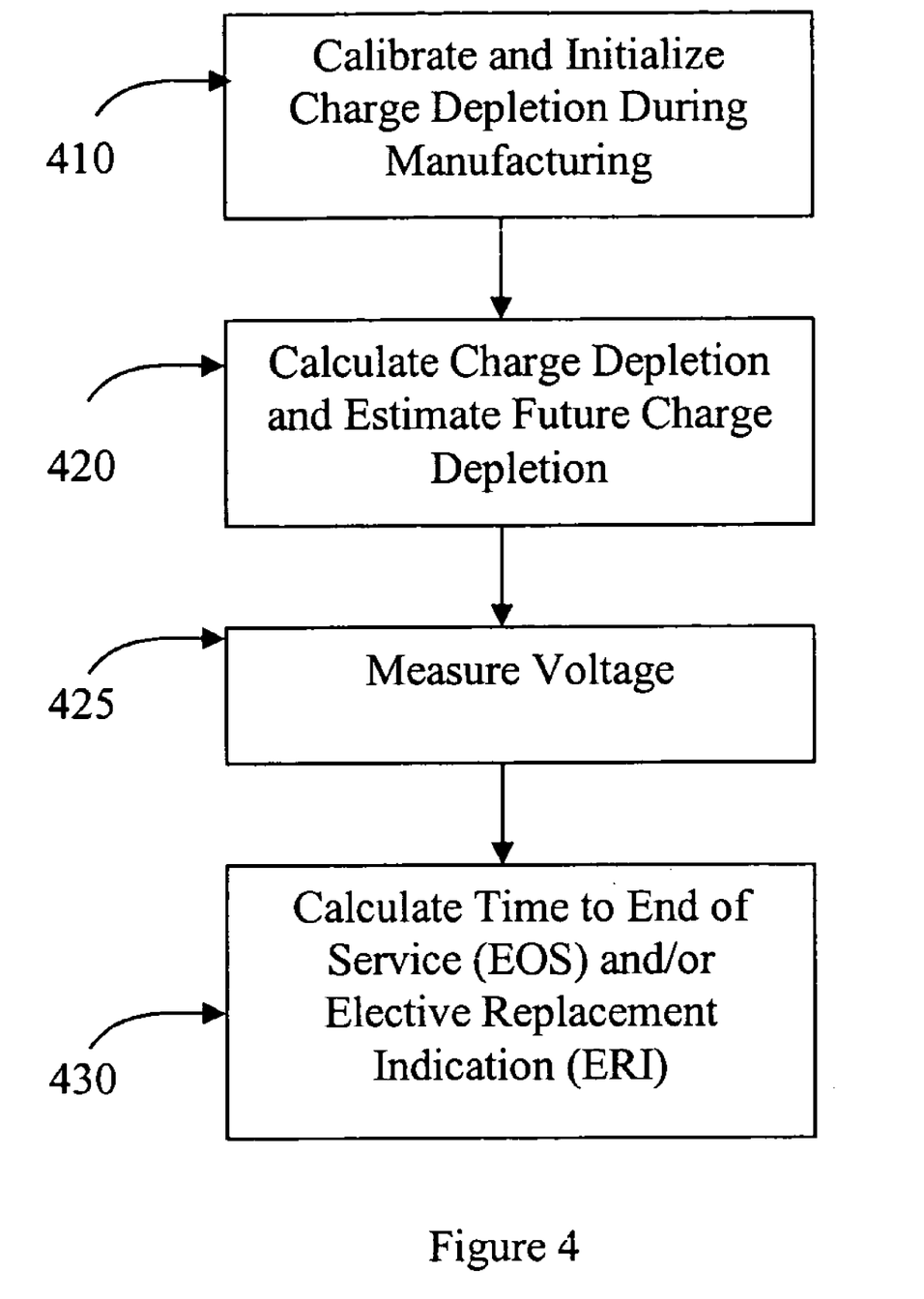
FIG. 4 is a flowchart representation of a method of providing a warning signal relating to a power supply of the implantable medical device, in accordance with one illustrative embodiment of the present disclosure.

Consistent with the foregoing, FIG. 4 provides a flowchart depiction of a method for determining the remaining time to EOS and/or ERI based on known or determined IMD characteristics such as battery charge or voltage and present usage rates, depending on where in its useful life the battery is operating. In one embodiment, the present usage of the IMD 110 is calibrated during manufacture (step 410). Current drawn by the IMD from the battery is defined as electrical charge per unit time. The total charge depleted from the battery as a result of the operations of the IMD may be determined by multiplying each distinct current rate used by the IMD by its respective time used. In one embodiment, as part of the calibration, during manufacturing, a power supply capable of generating known currents and voltages may be used to characterize the power consumption or current depletion of the implantable medical device 110 during its stimulation and idle modes. The power consumption data thus obtained is preferably stored in a memory of the IMD.

Once the charge usage characteristics of the IMD are known, the battery may be subsequently installed into the implantable medical device 110 for operation and thereafter a record of power consumed by the implantable medical device 110 is maintained. In a particular embodiment, the calibration step 410 involves calibration of present usage for idle periods ($r_i$) and stimulation periods ($r_s$) of the device. Current may thus be used as a proxy value for electrical charge depletion, and the calibration step allows a precise determination of the amount of electrical charge used by the device after implantation. As used herein, the terms "depletion rate," "consumption rate," and "usage rate" may be used interchangeably, unless otherwise indicated, and refer to the rate at which electrical charge is depleted from the battery. However, as noted above, current may be used as a proxy for electrical charge, and where this is the case, current rates $r_i$ and $r_s$ may also be referred to as "present usage," "current rate," "current consumption," "charge depletion," "depletion rate" or similar terms.

As previously noted, the IMD 110 has a number of settings and parameters (e.g., current, pulse width, frequency, and on-time/off-time) that can be changed to alter the stimulation delivered to the patient. These changes result in different usage rates by the IMD 110. In addition, circuit variations from device to device may also result in different present usage rates for the same operation. Calculations and estimations are preferably performed during the manufacturing process in order to calibrate accurately and precisely the present usage rates of the IMD 110 under a variety of stimulation parameters and operating conditions. A calibration of the present usage rates and a determination of the charge present on the battery at the time of implant allow a more accurate assessment of actual and predicted charge depletion after the IMD 110 is implanted. The initial charge on the battery may include a safety factor, i.e., the charge may be a "minimum charge" that all batteries are certain to possess, even though many individual batteries may have a significantly greater charge. Nothing herein precludes a determination of a unique initial charge for each individual battery. However, it will be recognized that such individual determinations may not be economically feasible. A more detailed illustration and description of the step (410) of calibrating present usage and initializing the battery charge for the implantable medical device 110 is provided in FIG. 5 and the accompanying description below.

After calibrating the present usage characteristics of the IMD 110, the IMD may be implanted and subsequently a charge depletion calculation is performed (step 420). In an embodiment, the charge depletion calculation is performed periodically, or in an alternative embodiment, the charge depletion calculation is performed each time the external unit 150 is in communication with the IMD 110. This calculation may be performed by the IMD itself, the external unit 150, or by both, and includes determining the actual electrical charge depleted from the battery 210 and estimating current consumption (i.e., depletion rates), which may, depending on where the battery is operating within its useful life, be used to calculate an elective replacement indication (ERI) and/or an end of service (EOS) signal (step 430). A more detailed illustration and description of the step 420 of calculating the electrical charge depleted is provided in FIG. 6 and the accompanying description below. In step 425, the voltage across the battery unit 210 is measured to determine whether the battery unit 210 is operating at a voltage greater than, equal to, or less than a voltage associated with the knee, or transition point of non-linearity in the battery voltage depletion curve (as shown in FIG. 3). In step 430 an estimated time until an elective replacement indication will be generated and/or the estimated time until the end of service are calculated based on whether the battery unit 210 is operating at a voltage greater than, equal to, or less than a voltage associated with the knee. A more detailed description and illustration of the step 430 of calculating the time to ERI and/or EOS is provided in FIG. 7 and the accompanying description below.

Figure 5:
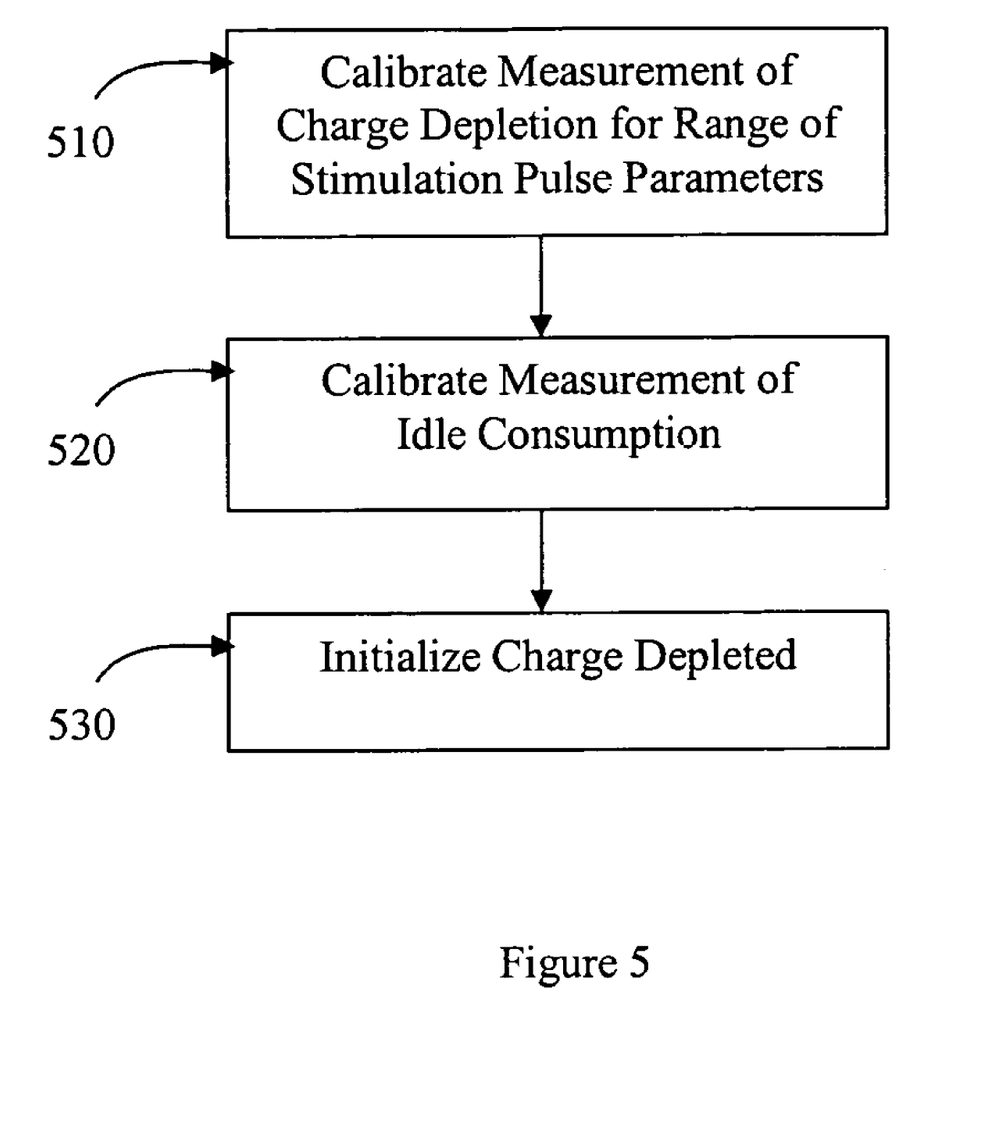
FIG. 5 is a flowchart representation of a method of performing a calibration of a charge depletion tabulation, in accordance with one illustrative embodiment of the present disclosure.

Referring now to FIG. 5, a flowchart diagram is provided depicting in greater detail the step 410 (FIG. 4) of calibrating and initializing the IMD 110 during manufacturing. In one embodiment, the current rates for the IMD 110 during stimulation are calibrated (block 510). During manufacturing, several different combinations of measurements may be calibrated. More specifically, measurements of charge depletion relating to different types of pulses (i.e., pulses having different stimulation parameters) are calibrated to ensure that present usage measurements for the IMD are accurate over a wide range of stimulation parameters. In other words, various pulses having a range of current amplitudes, pulse widths, frequencies, duty cycles and/or lead impedances into which the pulses are delivered are used to calibrate the measurement of present usage during stimulation to establish a baseline of the measurement of charge depletion for various types of pulses. All operational variables relating to or affecting the present usage rates of the IMD may be considered.

More particularly, during manufacture of the IMD 110, several combinations of data points relating to various current rates resulting from various combinations of pulse parameters are used in one embodiment to generate an approximately linear equation that relates various pulse parameters to current rate, which may then be used to determine charge depletion when the battery unit 210 is operating at a voltage greater than or equal to the voltage associated with the knee. For example, for a first stimulation, pulses of a certain frequency are provided and for a second stimulation, the frequency of the pulses used may be doubled. Therefore, the estimated present usage rate for the second stimulation may be estimated to be approximately double that of the power consumption or charge depleted due to the first stimulation. As another example, a first stimulation may be of a first pulse width and a second stimulation may be of a pulse width that is double that of the width of the first pulse. Therefore, a relationship between the pulse width to the current consumption of the second pulse may be estimated to be approximately double that of the present usage rate of the first pulse. In one embodiment, a graph may be generated using the various types of stimulation versus the current consumption associated with that stimulation.

As yet another example, a first stimulation pulse may have a first current amplitude and a second stimulation pulse may have a current amplitude that is double that of the first stimulation pulse. Therefore, the current consumption of the second stimulation pulse may be estimated to be approximately double that of the current consumption of the first stimulation pulse. The power consumption is directly proportional to the current consumption. Therefore, a relationship of a pulse parameter to present usage rate may be estimated or measured such that an interpolation may be performed at a later time based upon the linear relationship developed during the calibration of the power consumption during stimulation. It may be appreciated that the relationships of some pulse parameters to present usage rate may not be a simple linear relationship, depending upon such pulse characteristics as the type of pulse decay (i.e., square wave, exponential decay), for example. Nevertheless, calibration of present usage rate for various pulse parameters may be performed by routine calculation or experiment for persons of skill in the art having the benefit of the present disclosure.

Referring again to FIG. 5, present usage during an idle (i.e., non-stimulating) period is calibrated in step 520. From the idle current consumption and the stimulation current consumption calibration, the overall current consumption may be modeled based upon programmed settings. It should be noted that while the disclosure as shown in the drawings describes a device having two present usage patterns associated with an idle period and a stimulation period, such a two-state embodiment is described solely for clarity, and more complex embodiments are possible involving a third state such as, by way of non-limiting example, a present usage rate associated with electrical sensing of the lead electrodes, which may be defined by a third current rate $r_3$. Four-state or even higher state embodiments are possible, although where the differences in present usage rates are small, or where a particular present usage rate comprises only a tiny fraction of the overall time of the device, the complexity required to implement and monitor the time such current rates are actually used by the device may render the device impractical. These multi-state embodiments may be implemented if desired, however, and remain within the scope and spirit of the present disclosure.

Using the calibration of present usage during stimulation periods (step 510) and idle periods (step 520), a calculation may optionally be made to initialize the charge depleted, if any, during manufacturing operations, such as the charge depleted during testing of the device after assembly (block 530). In a preferred embodiment, all of the calibrations are performed with a calibrated current source device, and not a battery, and in this case there is no charge depletion during manufacturing operations. In another embodiment, the amount of charge depleted during manufacturing may be small, in which case the initialization procedure may also be omitted. The calibration and/or initialization steps of FIG. 5 allow the IMD 110, via power-source controller 220, to maintain a running tally of how much charge has been depleted from the device. When the battery unit 210 is first inserted into the implantable medical device 110, the charge depleted is generally initialized to zero so that a running tabulation may begin from zero for maintaining a running tally of the charge depleted from the battery over the life of the implantable medical device 110. In one embodiment, the charge depleted tally is incremented throughout the operating life of the device and at any point the running tally may be subtracted from the known initial charge of the battery to determine the remaining charge. In an alternative embodiment, the charge depleted tally could be initialized to the value of the battery initial charge and the tally decremented throughout the device operation and directly used as the remaining charge. In either implementation, information relating to the baseline charge remaining on the battery at the end of manufacturing may be retained to calculate the estimated time to EOS or ERI when the battery is operating at a voltage greater than or equal to the voltage associated with the knee.

Figure 6:
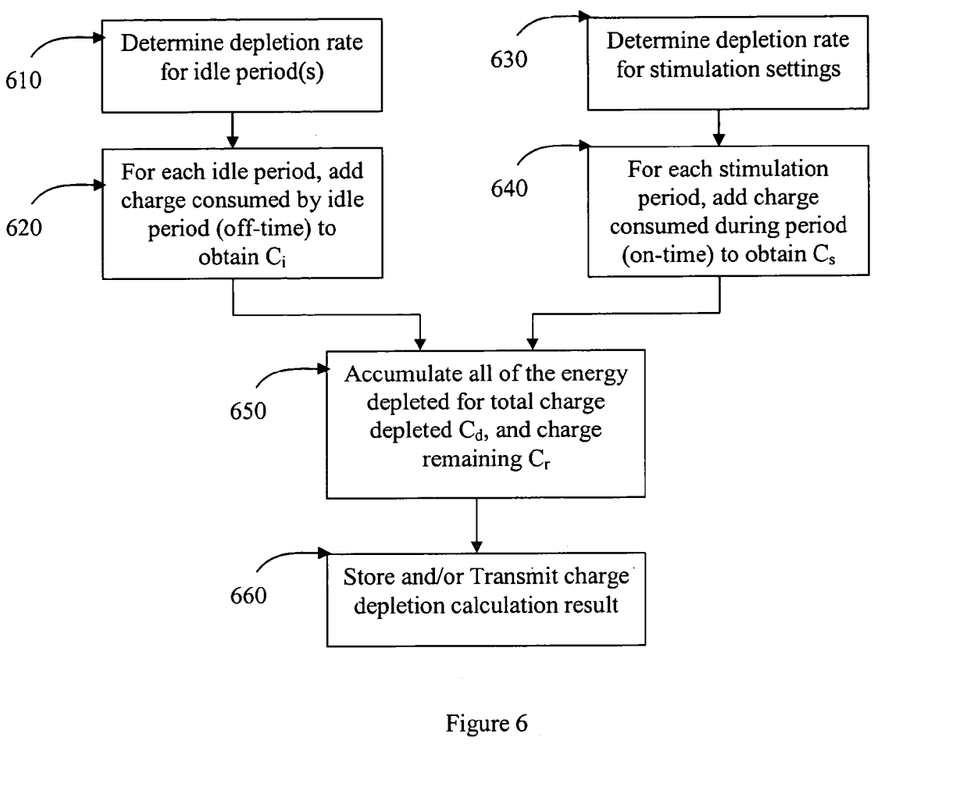
FIG. 6 is a more detailed flowchart illustrating a method of performing the charge depletion calculation indicated in FIG. 4, in accordance with one illustrative embodiment of the present disclosure.

Turning now to FIG. 6, a flowchart depiction of the step 420 of calculating charge depleted by the device is provided in greater detail. For simplicity, only the two-current state of a single idle period and a single stimulation period is shown. Embodiments having additional present usage rates are included in the present disclosure. The IMD 110 may determine a current depletion rate $r_i$ for idle periods (block 610). The rate is preferably stored in memory. In one embodiment, the determination is made by the IMD 110 after implantation. In a preferred embodiment, the idle current depletion rate may be a rate determined during manufacturing (i.e., a rate calibrated in step 520) and stored in the memory 280. An idle period is defined as a time period when the implantable medical device 110 is not performing active stimulation, i.e., is not delivering a stimulation pulse to the electrodes. Various electronic functions, such as tabulation and calculation of numbers or execution of various software algorithms within the IMD 110 may take place during the idle period.

As noted, the current rate $r_i$ during idle periods 610 may be predetermined during the manufacturing process (step 520) and may include various considerations, such as the power consumption of the operation of various electronics in the implantable medical device 110, even though no active stimulation may be taking place during that time period. However, since the implantable medical device 110 may be occasionally reprogrammed while still implanted inside a patient's body, the number and duration of idle periods may vary according to the duty cycle and frequency of the stimulation pulses. Therefore, the IMD 110 (e.g., via the power source controller 220 in the device) may maintain a running tabulation of the idle periods, and for each idle period a certain amount of charge depleted during the idle period (i.e., off time) is tabulated and stored in memory 280 (step 620).

It will be appreciated that the depleted charge may be obtained in a number of different ways, each within the scope of the present disclosure. Specifically, the total time of all idle periods since implantation, initialization, or since a previous idle power depletion calculation, may be maintained as a running total idle time in memory, or alternatively a running tally of charge depleted during idle periods may be maintained. While these values are different numerically, they are directly related by simple equations as discussed more fully hereinafter. At an update time, the total idle time may be periodically accessed and multiplied by the idle period present usage rate to determine the total power depleted during idle periods since implantation, initialization, or the previous calculation.

The IMD 110 may also maintain in memory 280 a tabulation of present usage rates (i.e., charge depletion) for a wide range of stimulation settings (step 630). In another embodiment, theoretical charge depletion calculations relating to particular types of stimulation may be provided to the IMD 110. The stimulation parameter settings may then be used by the device to maintain a running tabulation of the charge depleted during stimulation periods using a present usage rate $r_s$ calculated from the pulse width, pulse amplitude, pulse frequency, and other parameters which may impact the present usage rate. This method provides specific present usage rates for a variety of stimulation parameter settings and lead impedances without requiring the storage of present usage rates for all possible stimulation parameter settings and lead impedances.

In one embodiment, the charge depleted may be stored in micro-amp seconds; however, various other measurement units may be utilized. In one embodiment, the IMD 110 itself may be capable of calculating the present usage rate for a particular combination of programmed output settings based upon a known relationship between present usage rates and different combinations of programmed settings. The relationship may then be used to interpolate a particular present usage rate for a particular combination of programmed output settings. However, in order to reduce the computation load on the device, some or all of these calculations, including the interpolation, are preferably performed by an external programmer 150. Therefore, upon programming or performing routine maintenance of the implantable medical device 110, the external unit 150 may perform the calculations to determine the present usage rate during future stimulation cycles based upon the settings implemented during the programming or maintenance operation.

For example, if the stimulation for a particular patient is set to a particular pulse width, the external device 150 may factor in the calibration data and determine a present usage rate for a particular set of stimulation settings. Therefore, for each stimulation period, the charge that is depleted is tabulated for the stimulation period ("on-time") by multiplying the stimulation time by the present usage rate and a running tabulation is maintained (block 640). For example, if the predetermined present usage rate for each second of stimulation at a particular combination of parameter settings is 100 microamps, and the stimulation is 30 seconds long, a calculation is made by multiplying the 30 second time period for the stimulation, by the 100 microamps to arrive at 3000 micro amp seconds of charge consumed, which is then added to a running charge consumption tally.

As illustrated in FIG. 6, the sum of the tabulations of the charge depleted for the idle period (off-time or inactive period; step 620) and the charge depleted for the stimulation period (on-time or active period; step 640) are added to arrive at a total charge depleted by the IMD 110 (block 650). It will be appreciated that the sum of idle period and stimulation charge depletion may occur at the conclusion of one or more cycles of idle period and stimulation period, or continuously throughout idle periods and stimulation periods. Occasionally during the operational life of the IMD 110, various stimulation parameters may be changed to provide different types of stimulation. However, utilizing the steps described herein, a running tally (or a periodically updated tally) of the charge depletion is maintained, such that even when the stimulation settings change, the device maintains a substantially accurate reflection of the actual charge that has been depleted by the IMD 110, and future depletion calculations are based on the depletion rate for the newly programmed settings.

The memory 280 may store the results of the charge calculations (step 660). The data stored may include both the present usage rates for idle and stimulation periods of the IMD 110, as well as the total charge depleted. This data may be utilized by the IMD 110 and/or external unit 150 to determine various aspects of the device, including the time remaining until an ERI is generated, or the time remaining until EOS.

The calculations associated with steps 620, 640 and 650 may be expressed mathematically. In particular, the total charge available from the battery $C_{tot}$ after it is placed in the IMD 110 may be represented as the difference between an initial battery charge $C_{initial}$ and the EOS battery charge $C_{EOS}$, as expressed in Equation 1.

$$C_{tot} = C_{initial} - C_{EOS} \quad (Eq. 1).$$

The charge depleted by the IMD 110 during idle periods $C_i$ (step 620) may be expressed as the idle period present usage rate $r_i$ multiplied by the total duration of all idle periods $\Delta t_i$ according to equation 2.

$$C_i = r_i \times \Sigma \Delta t_i \quad (Eq. 2).$$

Where multiple idle rates are present, the above equation will be solved for each idle present usage rate and the results summed to obtain $C_i$. Similarly, the charge depleted during stimulation periods $C_s$ (step 640) may be expressed as the stimulation period present usage rate $r_s$ multiplied by the total duration of all stimulation periods $\Delta t_s$ according to equation 3.

$$C_s = r_s \times \Sigma \Delta t_s \quad (Eq. 3).$$

Again, where multiple stimulation rates are used the equation will be solved for each stimulation rate and the results summed. The total charge depleted $C_d$ is the sum of $C_i$ and $C_s$, as shown in equation 4.

$$C_d = C_i + C_s \quad (Eq. 4).$$

Finally, the charge remaining until EOS ($C_r$) at any arbitrary point in time is the difference between the total energy or charge available $C_{tot}$ and the charge actually depleted from the battery $C_d$ at that same point in time, as expressed in equation 5 (step 650).

$$C_r = C_{tot} - C_d \quad (Eq. 5).$$

This may be accomplished by counters that record the amount of time the device uses the idle present usage rate(s) and the stimulation present usage rate(s), respectively, which are then multiplied by the applicable present usage rate to obtain the total consumed charge during the idle and stimulation periods. Alternatively, separate registers may directly maintain a running tally of the charge depleted during stimulation periods and idle periods, respectively.

Figure 7:
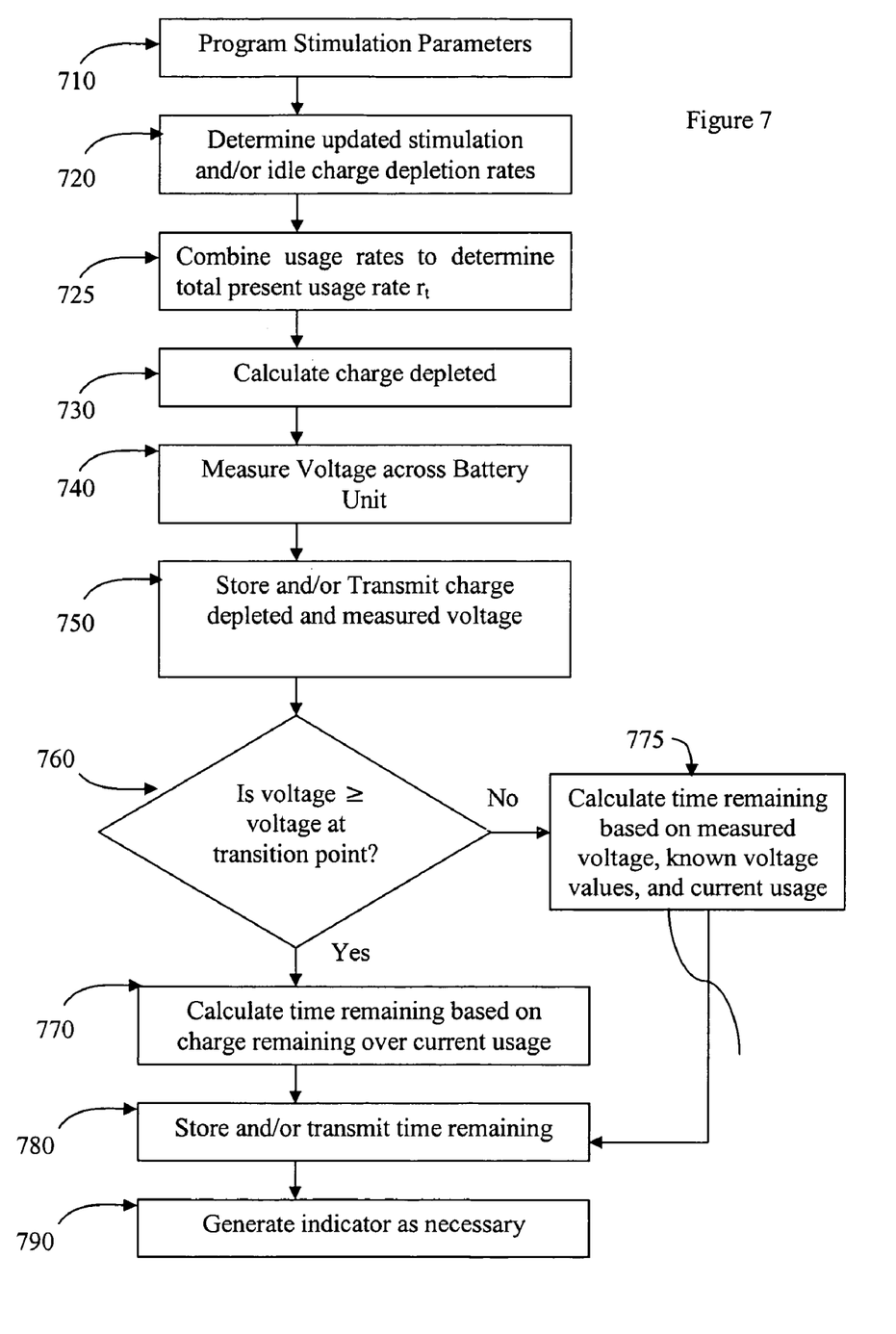
FIG. 7 is a more detailed flowchart illustrating a method of performing an end-of-service (EOS) and/or an elective replacement indication (ERI) determination, as indicated in FIG. 4, in accordance with one illustrative embodiment of the present disclosure.

Turning now to FIG. 7, a more detailed flow chart depicting the calculation of the time to the end of service (EOS) and/or elective replacement indicator (ERI) signals, as indicated in step 430 of FIG. 4, is illustrated. The IMD 110 is programmed for delivering to the patient electrical pulses having predetermined parameters (step 710). Programming the stimulation settings may be performed during manufacturing and/or by a healthcare provider when the external unit 150 communicates with the IMD 110. Occasionally, medical personnel may determine that an alteration of one or more of the stimulation parameters is desirable. Implementation of such changes may easily be accomplished to optimize the therapy delivered by the IMD. Alternatively, as part of a routine diagnostic process, a predetermined change to the stimulation settings may be performed. Additionally, the IMD 110 may have multiple sets of stimulation parameters stored in memory and may switch between the different stimulation modes represented by those parameters at preset times or at the occurrence of certain physiological events. When a change in one or more stimulation parameter settings is implemented (whether by programming or accessing data from memory), the IMD 110 and/or the external unit 150 may determine an updated stimulation period present usage rate $r_s$ associated with the new parameter settings, and subsequent updates to the total charge consumed will be based upon the new stimulation period present usage rate (step 720). The rates may either be stored in memory or calculated from an equation by interpolation among known current rates for known parameter settings, as previously described. It is also possible that changes to the software or firmware of the device could change the idle period depletion rate, in which event a new idle period present usage rate $r_i$ may also be calculated and reflected in subsequent calculations of total charge depleted (step 720).

Because the duty cycle (on-time to off-time ratio) is also a programmed parameter, the present disclosure allows both the idle period present usage rate ($r_i$) and the stimulation period present usage rate ($r_s$) to be combined into a single rate for purposes of projecting future energy or charge depletion and calculating a time to EOS and/or ERI. This rate represents the total present usage rate ($r_t$) of the device (step 725). Following updates to the stimulation and/or idle period present usage rates $r_s$ and $r_t$, the updated rates are then used to calculate a new total charge remaining $C_r$, by a method substantially as shown in FIG. 6 and previously described (step 730).

Additionally, the voltage across the battery unit is measured (step 740). In an embodiment, the voltage across the battery may be measured periodically while in an alternative embodiment, the voltage across the battery is measured when the IMD 110 is in communication with the external unit 150. The measured voltage across the battery in step 740 and the charge depleted in step 730 are stored in a memory in the IMD 110 and/or transmitted from the IMD 110 to the external unit 150 for storage in a memory in the external unit 150 (step 750).

Once the total charge remaining and measured voltage across the battery unit are retrieved from memory, the remaining time to an activation of an EOS is calculated depending on where in the battery's useful life it is operating. A comparison of the measured battery voltage and the voltage associated with the knee is performed to see whether the measured battery voltage is greater than or equal to the voltage associated with the knee (step 760).

When the measured voltage across the battery unit is greater than or equal to the voltage associated with the knee, the time remaining is calculated by dividing the remaining charge by the total depletion rate as shown in Equation 6 (Step 770).

$$t = (C_r)/(r_t) \quad \text{(Eq. 6)}.$$

Equation 6 may be expressed in more discrete terms as shown in Equation 7.

$$t = (C_{initial} - C_{EOS} - C_d)/I_{avg} \quad \text{(Eq. 7)}.$$

Wherein $I_{avg}$ is the current consumption rate (i.e., estimated future depletion rate) based upon the IMD's present settings. Alternatively, $I_{avg}$ may be based on proposed settings, as desired, to estimate the time until EOS impact of altering one or more of the settings. Generally speaking, $I_{avg}$ is not a constant, but varies from one generator to the next, and also varies with the program settings.

When the measured voltage across the battery unit is less than the voltage associated with the knee, the time remaining is calculated by dividing the product of the difference between the measured voltage ($V_{bat}$) and a voltage associated with the EOS ($V_{EOS}$ 312), the initial charge ($C_{initial}$), and a percentage of battery capacity typically remaining at the knee (% knee) by the product of the average current ($I_{avg}$) and the different between the voltage associated with the knee ($V_{knee}$ 310) and the voltage associated with the EOS ($V_{EOS}$ 312), as shown in Equation 8 (Step 775).

$$t = \{(V_{bat} - V_{EOS}) \times \%_{knee} \times C_{initial}\}/\{I_{avg} \times (V_{knee} - V_{EOS})\} \quad \text{(Eq. 8)}.$$

Applying Equation 8 regardless of where the battery is along the battery voltage depletion curve results in accuracy only in the last negative slope region of battery life, and inaccuracy in the range of voltages greater than the voltage associated with the knee, which is why it is advantageous to use Equation 7 at measured voltages greater than or equal to the voltage associated with the knee and Equation 8 at measured voltages less than the voltage associated with the knee. Equations 7 and 8 may be combined, for clarity's sake, into a single, non-linear equation, as shown in Equation 9.

$$T_{EOS}(x) = \begin{cases} \dfrac{(C_{initial} - C_{EOS} - C_d)}{I_{avg}} & x \geq V_{knee} \\ \dfrac{(V_{bat} - V_{EOS}) \times \%_{knee} \times C_{initial}}{I_{avg} \times (V_{knee} - V_{EOS})} & x < V_{knee} \end{cases} \quad \text{(Eq. 9)}$$

Applying Equation 9 assures accuracy in the ranges of voltages greater than, equal to, and less than the voltage associated with the transition point of non-linearity in the battery voltage depletion curve.

The time remaining calculated in Step 770 or 775 may be stored in a memory of the IMD 110, or alternatively may be stored and/or transmitted to the external unit 150 (step 780). At a predetermined time period before the end of service of the battery unit 210 is reached, an ERI signal, which may prompt the healthcare provider and/or the patient to schedule elective replacement of an electronic device, may be asserted to provide a warning as necessary (Step 790). ERI is typically determined as simply a predetermined time, for example from 1 week to 1 year, more typically 6 months, earlier than EOS. In an alternative embodiment, the ERI signal may be defined as a particular charge level remaining ($C_{ERI}$) above the EOS charge, $C_{EOS}$. In this embodiment, the time period remaining until the ERI signal could be calculated by dividing $C_{EOS}$ by the total depletion rate $r_t$ and subtracting the resulting time period from the time to EOS as calculated in equation 6.

The time to EOS provides a warning to the healthcare provider and/or patient that the energy or charge supply will be depleted very shortly. Therefore, the time to EOS is reported to the implantable medical device 110 and/or to the external device 150 (block 740). The ERI is also reported to the implantable medical device 110 and/or to the external device 150, which is then brought to the attention of the patient and/or a medical professional.

The accuracy of the estimate of time remaining until EOS or until the generation of an ERI may be further refined by adding higher order terms to either of the linear equations 7 or 8. In various embodiments, the non-linear battery voltage depletion curve may be more accurately approximated by a higher order polynomial equation. In various embodiments, the second region of the battery voltage depletion curve may be more accurately approximated by a higher order polynomial equation, while the first region of the battery depletion curve is approximated by either a linear approximation or a non-linear, higher order polynomial equation. The equation for time remaining may be thus improved, reflecting the more accurate voltage curve (or portion of the voltage curve) of a higher order, and resulting in a more accurate calculation of the estimate of time remaining until EOS. A polynomial fitting software application employing any curve fitting technique, e.g., a least-squares fit, a LOESS (local polynomial regression fitting) function, or the like, may be run on a data set empirically obtained to approximate the battery voltage depletion curve with a polynomial equation of at least Nth degree, of the form: $f(x) = a_0 + a_1 x + \ldots + a_{n-1} x^{n-1} + a_n x^n$. In an embodiment, the polynomial equation approximating the battery voltage depletion curve is of at least the $2^{nd}$ degree.

A further refinement to the estimation of time remaining until EOS or until the generation of an ERI is to use a variable $V_{knee}$, rather than a constant $V_{knee}$ 310. In such an embodiment, $V_{knee}$ is a variable function of, for example, $I_{avg}$, rendering Equation 9 a multi-variable, non-linear equation. $V_{knee}$ 310 is the voltage associated with the knee, or transition point of non-linearity along the battery voltage depletion curve. The precise voltage along the curve where the actual transition takes place may vary with the programmed settings and $I_{avg}$. For simplicity's sake, the $V_{knee}$ 310 may be chosen and set as a constant value within the range of possible $V_{knee}$ values for the various programmed settings, determined experimentally. For example, in an embodiment, $V_{knee}$ 310 may be predetermined and set to a voltage of 2.6 volts. However, the $V_{knee}$ value 310 used in the time calculation (Eq. 9) may also be permitted to vary with $I_{avg}$ and program setting changes for a greater degree of accuracy in the estimate of time remaining until EOS.

In some embodiments, $V_{bat}$ is modified prior to use in EOS or ERI calculations based on temperature of the battery. In batteries such as those used in IMDs as disclosed herein, the voltage across the battery is impacted by extreme temperatures. Prior to implant, the value for $V_{bat}$ that is reported may adversely affect the estimate of time remaining until EOS. Specifically, the $V_{bat}$ reported in very cold temperatures, such as those an IMD might be exposed to during shipping and/or storage, is lower than the true voltage across the battery. As such, the time remaining until EOS calculated based on such an inaccurate $V_{bat}$ is a much shorter time than the IMD actually has remaining, which may result in a physician discarding an IMD prematurely. Thus, shipment or storage in cold temperature may result in IMD units not being used, as thought to be too near the end of service, when the $V_{bat}$ is artificially low.

In order to modify $V_{bat}$ to correct for any adverse effects of extreme temperature, the temperature is measured and the $V_{bat}$ value is automatically corrected by a known amount corresponding to the temperature. Generally, there is an approximately linear relationship between the temperature and the number of volts necessary to correct $V_{bat}$ for temperature, thus the correction factor may be directly related to the measured temperature. Alternatively, the relationship between the temperature and number of volts necessary to correct $V_{bat}$ for temperature may be approximated by a higher order polynomial equation, and as is well known in the art, a higher order equation may be solved to calculate the proper amount of voltage to add in order to correct $V_{bat}$.

Rather than actually correcting the $V_{bat}$ value for temperature, the temperature may be communicated to a user of the external unit 150, such as a physician, to give notice to the physician or other user of the external unit 150 that the temperature of IMD unit should be permitted to stabilize in an environment similar in temperature to the environment the IMD is in when implanted. By first permitting the IMD's temperature to stabilize, the time remaining to EOS may be re-evaluated with a more accurate value for $V_{bat}$ once the temperature is no longer extreme.

A further refinement to the estimation of time remaining until EOS or until the generation of an ERI is modifying the $V_{bat}$ prior to use in calculations with a constant factor, depending on where the battery is operating within its useful life. Specifically, in batteries such as those used in IMDs 110 such as that of the disclosure, the battery may report an artificially low voltage due to the internal battery impedance that later in the battery's useful life has little to no impact on the reported voltage. The internal battery impedance has an impact on the reported battery voltage typically in the first 2% of the battery's useful life, but may affect the reported battery voltage for up to around the first 7-8% of the battery's useful life. The IMD 110 may alter the $V_{bat}$ value communicated to the external unit 150 for more accurate calculation of the time remaining to EOS, or alternatively, the $V_{bat}$ value used internally to the IMD 110 to more accurately calculate the time remaining to EOS. The battery voltage may, in an embodiment in which the $V_{bat}$ value is corrected in the early portion of its life, be governed by Equation 10.

$$V_{bat} = \begin{cases} V_{bat} + C_{const} & \text{For } (V \geq 2.45 \text{ volts}) \& (C_d \leq 7.5\%) \\ V_{bat} & \text{For } (Vbat < 2.45 \text{ volts}) \text{ or } (C_d > 7.5\%). \end{cases} \quad \text{(Eq. 10)}$$

The correction factor amount $C_{const}$, introduced by Equation 10, injects a non-linear nature into the battery voltage value, thereby introducing non-linearity into the entire algorithm represented by Equation 9. The constant $C_{const}$ may be set during manufacture, according to calibration and characteristics known about the battery, such as its characteristic internal battery impedance at the beginning of its useful life. In order to correct for the internal battery impedance inaccuracy in the preferred embodiment, $C_{const}$ is set for at least 0.25 volts, and preferably for 0.5 volts. As can be seen from Equation 10, once the battery is no longer in the earliest portion of its useful life and the effects of the internal battery impedance on battery voltage have lessened, the value for $V_{bat}$ is generally accurate enough so as to not require adding the correction factor.

Utilizing embodiments of the present disclosure, a more accurate assessment of the status of the battery may be assessed, thereby providing better warnings to the user and/or to a healthcare provider assessing the operations of the IMD 110. Various end of service signals (EOS) and/or elective replacement indication (ERI) signals may be provided to indicate the status of the operation of the IMD 110. In an embodiment, an ERI signal may be generated when there are six months left until EOS, according to the calculations discussed herein.

The particular embodiments disclosed above are illustrative only, as the disclosure may be modified and practiced in different but equivalent manners apparent to those skilled in the art having the benefit of the teachings herein. Furthermore, no limitations are intended to the details of construction or design herein shown, other than as described in the claims below. The particular embodiments disclosed above may be altered or modified and all such variations are considered within the scope and spirit of the disclosure. Accordingly, the protection sought herein is as set forth in the claims below.

What is claimed is:

1. An implantable medical device, comprising:
   an energy storage device that provides power for an operation performed by the implantable medical device, characterized by a non-linear battery voltage depletion curve of voltage over time;
   a stimulation unit operatively coupled to the energy storage device that provides an electrical signal; and
   a controller operatively coupled to the stimulation unit and the energy storage device, the controller comprising:
     a charge depletion determination unit that determines an electrical charge depleted by the energy storage device during operation of the implantable medical device;
     a voltage determination unit that determines whether a measured voltage across the energy storage device has reached a transition voltage; and
     a useful life determination unit that determines a time period remaining in the energy storage device's useful life based upon at least one of 1) a function of the electrical charge depleted, and 2) a function of the measured voltage;
   wherein the useful life determination unit determines the time period remaining in the energy storage device's useful life based on the function of the electrical charge depleted when a measured voltage across the energy storage device is greater than or equal to the transition voltage, and the useful life determination unit determines the time period until the end of service of the energy storage device based on the function of the measured voltage when the measured voltage across the energy storage device is less than the transition voltage;

wherein when the measured voltage is less than the transition voltage, the useful life determination unit calculates the time period remaining the energy storage device's useful life based upon the measured voltage, an end-of-service voltage, a percentage of energy storage device capacity remaining at a transition point of non-linearity in a battery voltage depletion curve representing the voltage across the energy storage device over time and at least one of the transition voltage, the total available electrical charge, and a consumption rate.

2. The implantable device of claim 1, wherein the transition voltage is a voltage associated with a transition point of non-linearity in the battery voltage depletion curve.

3. The implantable device of claim 2, wherein the transition voltage comprises a variable value based upon a consumption rate.

4. The implantable device of claim 1, wherein when the measured voltage is greater than or equal to the transition voltage, the determination unit calculates a time period remaining in the energy storage device's useful life based upon the total charge depleted, and at least one of the total available electrical charge and a consumption rate.

5. The implantable medical device of 1, wherein the controller generates at least one of (1) an end of service signal based upon a determination that the time period remaining in the energy storage device's useful life has already ended and (2) an elective replacement indicator signal based upon a determination that the time period remaining in the energy storage device's useful life is less than or equal to a predetermined period of time.

6. The implantable medical device of claim 5, wherein the predetermined period of time is approximately six months.

7. The implantable medical device of claim 1, further comprising a correction factor unit for adding at least one of (1) a first correction factor when the measured voltage is greater than or equal to a predetermined voltage, (2) a second correction factor associated with the energy storage device impedance, and 3) a third correction factor associated with a measured temperature of the energy storage device.

* * * * *